US009770521B2

(12) United States Patent
Selbekk et al.

(10) Patent No.: US 9,770,521 B2
(45) Date of Patent: Sep. 26, 2017

(54) ULTRASOUND CONTACT FLUID

(71) Applicant: Sinvent AS, Trondheim (NO)

(72) Inventors: Tormod Selbekk, Trondheim (NO);
Geirmund Unsgård, Skatval (NO)

(73) Assignee: Sinvent AS, Trondheim (NO)

(*) Notice: Subject to any disclaimer, the term of this patent is extended or adjusted under 35 U.S.C. 154(b) by 307 days.

(21) Appl. No.: 14/398,871

(22) PCT Filed: May 8, 2013

(86) PCT No.: PCT/EP2013/059588
§ 371 (c)(1),
(2) Date: Nov. 4, 2014

(87) PCT Pub. No.: WO2013/167654
PCT Pub. Date: Nov. 14, 2013

(65) Prior Publication Data
US 2015/0118161 A1  Apr. 30, 2015

(30) Foreign Application Priority Data
May 9, 2012  (NO) .................................. 20120529

(51) Int. Cl.
A61K 49/22 (2006.01)
A61B 8/08 (2006.01)

(52) U.S. Cl.
CPC ............ *A61K 49/22* (2013.01); *A61K 49/226* (2013.01); *A61B 8/0808* (2013.01)

(58) Field of Classification Search
None
See application file for complete search history.

(56) References Cited

U.S. PATENT DOCUMENTS

| 4,542,745 | A | 9/1985 | Oakley et al. |
| 5,625,137 | A | 4/1997 | Madsen et al. |
| 5,644,429 | A * | 7/1997 | Alfano .................. A61B 5/0091 359/559 |
| 6,302,848 | B1 | 10/2001 | Larson et al. |
| 6,475,800 | B1 | 11/2002 | Hazen et al. |
| 2005/0074407 | A1 | 4/2005 | Smith |
| 2009/0117052 | A1 * | 5/2009 | Wang .................. A61K 41/0052 424/9.5 |

FOREIGN PATENT DOCUMENTS

| CN | 101695576 A | 4/2010 |
| EP | 1 671 656 A1 | 6/2006 |
| EP | 1 842 559 A1 | 10/2007 |
| JP | H09-502173 A | 3/1997 |
| WO | 94/21301 A1 | 9/1994 |
| WO | 01/58344 A1 | 8/2001 |
| WO | 2008/137944 A1 | 11/2008 |
| WO | 2009/013692 A2 | 1/2009 |

OTHER PUBLICATIONS

Hippalgaonkar et al. Injectable lipid emulsions-advancements, opportunities and challenges. 2010 AAPS PharmSciTech. 11:1526-1540.*
Search Report for Norwegian Application No. 20120529, dated Dec. 6, 2012 (2 pages).
International Search Report for corresponding International Application No. PCT/EP2013/059588, mailed Jul. 23, 2013 (4 pages).
Written Opinion for corresponding International Application No. PCT/EP2013/059588, mailed Jul. 23, 2013 (6 pages).
International Preliminary Report on Patentability for corresponding International Application No. PCT/EP2013/059588, mailed Jul. 23, 2013 (13 pages).
Unsgaard G. et al.; "Intra-operative 3D ultrasound in neurosurgery;" Acta Neurochirurgica; The European Journal of Neurosurgery, Springer-Verlag, VI, vol. 148, No. 3; XP019377938; Mar. 1, 2006 (19 pages).
Anonymous; Product Information—Intralipid 10%, 20% and 30%, XP002702431; Retrieved from the Internet: URL: http://www.medsafe.govt.nz/profs/datasheet/i/Intralipidinf.pdf; May 18, 2010 (9 pages).
Office Action in counterpart Japanese Patent Application No. 2015-510813 issued on Dec. 21, 2016 (9 pages).

* cited by examiner

*Primary Examiner* — Michael G Hartley
*Assistant Examiner* — Jennifer Lamberski
(74) *Attorney, Agent, or Firm* — Osha Liang LLP

(57) ABSTRACT

An aqueous ultrasound contact fluid includes a pharmaceutical grade triglyceride and a pharmaceutically acceptable emulsifier and the use of the ultrasound contact fluid in an intraoperative or interventional ultrasound imaging procedure. A method for intraoperative ultrasound imaging includes filling an aqueous ultrasound contact fluid into a body cavity. The aqueous ultrasound contact fluid is a composition comprising a pharmaceutical grade triglyceride and a pharmaceutically acceptable emulsifier and optionally a pharmaceutically acceptable humectant, and the triglyceride content is in the range of 8-240 g/1000 ml composition contact fluid and the amount of emulsifier is 0.4-18 g/1000 ml composition contact fluid, and optionally a humectant in the amount of 1.2-30 g/1000 ml. The method further includes obtaining an ultrasound image of a body region that comprises at least part of the body cavity filled with the aqueous ultrasound contact fluid. The aqueous ultrasound contact fluid reduces image artifacts associated with the body cavity.

16 Claims, 3 Drawing Sheets

ULTRASOUND CONTACT FLUID

FIELD OF INVENTION

The present invention concerns an ultrasound contact liquid/gel and the use of said gel in intra surgical ultrasound imaging.

BACKGROUND OF INVENTION

Ultrasound imaging is widely used in medical examination, and is used in various clinical fields. Fluid or gel is used as an acoustic coupling in medical ultrasound imaging, and fluids with microbubbles/microspheres are used as ultrasound contrast agents. To ensure proper contact between the transducer/ultrasound probe and the skin/tissue to be examined a contact gel or liquid is used. The ultrasound contact gel is used to avoid air pockets between the transducer/probe and tissue, and to facilitate a good acoustic coupling between the surface of the ultrasound transducer and the tissue.

In many neurosurgical departments ultrasound is used for imaging of tumours in brain surgery. The purpose of ultrasound imaging is to locate the tumour and anatomical structures, as well as to identify residual tumour during surgery. High image quality should be sustained throughout the whole operation in order to monitor the progress of tumour resection. However, the progress of surgery may also cause more noise and more inaccurate display of the brain anatomy in the ultrasound images. The term artefact is in medical imaging used to describe any part of the image that does not accurately represent the anatomy of the subject being investigated, and it is well known that ultrasound is prone to several different types of artefacts. When using ultrasound in brain tumour surgery, the presence of artefacts may interfere the surgeon's interpretation of the images.

Ultrasound imaging is used in surgery, e.g. in neurological surgery i.e. brain surgery and heart surgery, to make sure that the damaged tissue, tumour etc. is completely removed, and that unnecessary resection healthy tissue is avoided. When contact gels or fluids are used in surgery particular requirements apply. The ultrasound contact gel must be sterile, non-toxic and easy to remove after use.

During brain tumour surgery a resection cavity is filled with saline water before ultrasound imaging, to enable propagation of sound and to prevent air artefacts. The difference in attenuation between brain and isotonic saline may cause artefacts that degrade the ultrasound images, potentially affecting resection grades and safety. The acoustic waves travel through the cavity filled with saline water before reaching the biological tissue. The attenuation of acoustic waves in saline water is very low compared to the attenuation of acoustic waves in biological tissue. The attenuation coefficient $\alpha$ for water is 0.0022 while for e.g. brain it is reported measured by various groups to be within approximately 0.4-1.0 (Duck F A, In *Physical properties of tissue*, Academic Press, LTD). A major component of the attenuation of sound in brain tissue is caused by absorption, in which part of the acoustic energy is converted to heat. These effects cause the acoustic waves propagating in saline water to have higher amplitudes than acoustic waves propagating an equal distance in biological tissue.

The total attenuation is estimated by the equation:

$$\text{Attenuation [dB]} = \alpha[\text{dB}/(\text{MHz}*\text{cm})]*l\,[\text{cm}]*f[\text{MHz}]$$

Wherein $\alpha$ is the attenuation coefficient $l$ is the medium length (or propagating distance)

$f$ is the frequency of the transmitted ultrasound wave

If we select a frequency of 8 MHz and a propagating distance of 10 cm and assume an attenuation coefficient of 0.8 for brain this will result in an attenuation of 0.18 dB for ultrasound propagating in water and an attenuation of 64 dB for waves propagating in brain. This difference in attenuation can generate noise in the ultrasound images e.g. when ultrasound is used intraoperatively in brain tumour surgery. The ultrasound waves transmitted through the water filled resection cavity will have a large amplitude when arriving at the cavity walls, due to the low attenuation of water. Thus, the sound waves being reflected from the cavity wall will also have relatively high amplitudes, see FIG. 1. Further, the sound waves propagating further into the tissue will have relatively high amplitudes. Compared to sound waves that have propagated entirely in brain tissue with a relative high attenuation coefficient, these transmitted and reflected waves will be less damped and thereby have significantly higher amplitudes. The fluctuations in intensity observed in the ultrasound images make it very difficult to interpret the images, see FIG. 1. The bright rim observed at the cavity wall may mask the presence of residual tumour, or the high intensity regions extending from the cavity wall may be interpreted as hyperechoic tumour when it actually is normal brain tissue.

The presence of the hyperechoic rim in ultrasound imaging of a resection cavity is described in several papers regarding the use of ultrasound in brain tumour surgery. This enhanced signal appearing below the fluid filled cavity in the ultrasound images is regarded as one of the major imaging artefacts encountered in peroperative ultrasound imaging. It is an objective of the present invention to reduce the enhancement artefact/brightness artefact/bright rim effect seen in ultrasound imaging of body cavities, thus substantially improving the usefulness of ultrasound imaging in e.g. resection monitoring. The brightness enhancement of tissue located beneath fluid filled spaces has been observed in ultrasound imaging of cysts, blood vessels or other fluid filled spaces. Because of this apparent enhancement of the reflected echo this frequently encountered image artefact is often referred to as brightness artefacts.

U.S. Pat. No. 6,302,848 concerns a medical ultrasound coupling media and lubricant, in gel or liquid form, comprised of polyethylene oxide (PEO), and aqueous solvent solutions. The inventive coupling media provides long-term biocompatibility (bio-inert, bio-erodible or biodegraded and excreted) in vivo with human tissue and body fluids. The ultrasound coupling and lubricating media is formulated and manufactured in such manner and form that renders the acoustic media sterile, non-cross-linked, pseudoplastic, and containing acceptably low levels of pyrogens.

EP 1 671 656 discloses an acoustic coupling agent comprising polyvinylpyrrolidone (PVP), which may be transported inside the body such as during surgery and with invasive procedures. It is disclosed that such coupling agent additionally comprises 1-99 weight % glycols, polyols and/or fats and esters thereof.

U.S. Pat. No. 5,625,137 discloses an ultrasound phantom for use with an ultrasound scanner where the phantom includes a low scatter tissue mimicking material. The material comprises an aqueous mixture of large organic water soluble molecules and an emulsion of fatty acid esters mixed with a hydroxy compound soluble in water.

CN 101695576, [abstract only] discloses a medical ultrasonic sterilization couplant, which is prepared from the following components in part by weight: sodium hydroxide 5-20, glycerol 150-450, ethylparaben 2-9, carbomer 10-50, chlorhexidine hydrochloride (CHX-HCL) 0.2-0.8, ethylene diamine tetraacetic acid (EDTA) 0.3-1.2, and distilled water 725-2,000. The couplant has a good acoustic matching and coupling function, avoids corroding and swelling ultrasonic probes, has disinfection and sterilization functions, avoids stimulating and sensitizing skin mucosae and can realize synchronous, quick and continuous disinfection and sterilization of the ultrasonic probes and the skin mucosae and effectively reduce potential intra-hospital cross infection risks caused by the contact of the ultrasonic probes (therapeutic heads) with human bodies in medical supersonic inspection and treatment processes. The couplant is applicable to trans-skin mucosa, transvaginal and transrectal ultrasonic diagnosis and treatment.

U.S. Pat. No. 4,542,745 reveals ultrasonic emulsion fluids which depending on the constitution provide emulsions with desired attenuation characteristics. The outer phase of the emulsion is a water and velocity enhancer mixture. Enhancers are suitable alcohols such as ethylene glycol, propylene glycol or glycerol. An oil phase such as a silicone fluid constitutes the suspended phase of the emulsion.

US 2005/074407 discloses an in vivo biocompatible and bio-excretable lubricant and ultrasound coupling fluid or gel comprising polyvinylpyrrolidone (PVP) and/or polyvinyl alcohol (PVA). The couplant fluid or gel comprises polyvinylpyrrolidone and/or polyvinyl alcohol solutions in water to which humectants such as alkylene glycols and/or polyalkylene glycols are added to achieve desired tactile and drying characteristics. Additionally, such fluids and gels may be prepared by addition of organic and inorganic cross-linkers.

SUMMARY OF THE INVENTION

Figure 1:
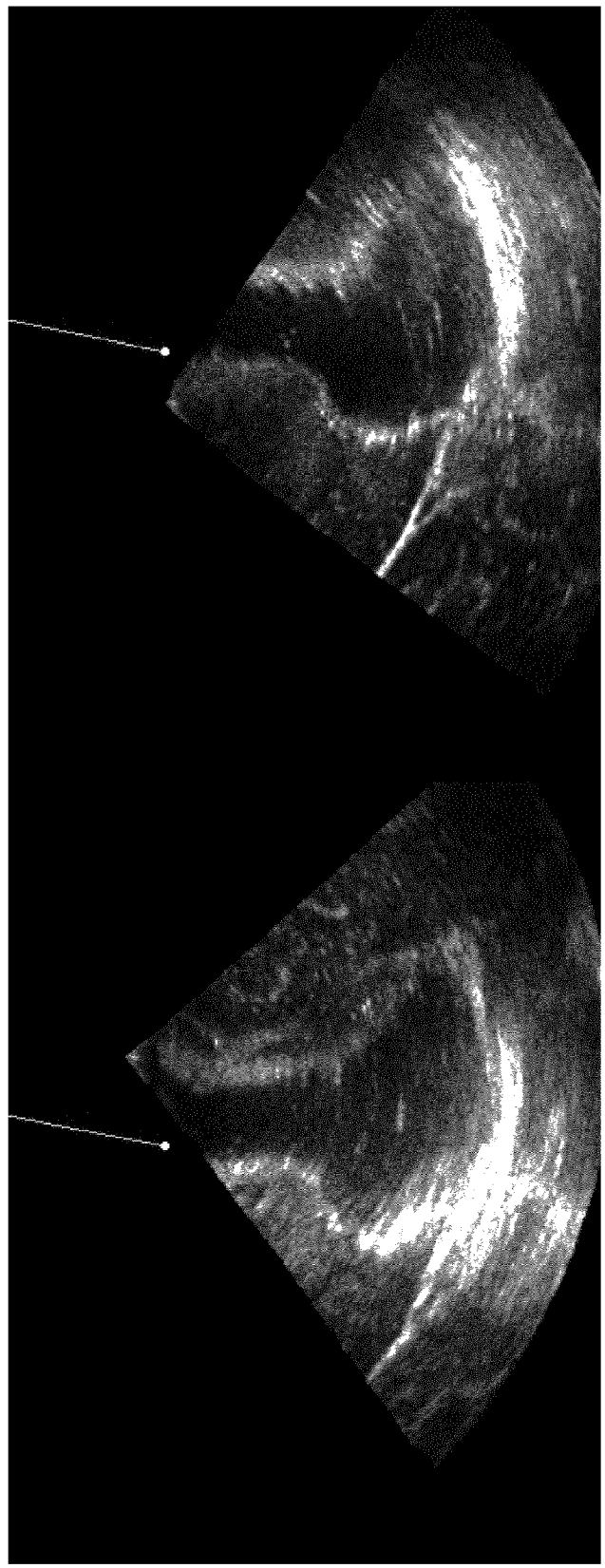
FIG. 1 shows reformatted image slices from 3D ultrasound volumes acquired intraoperatively as displayed on a navigation system. In the left image we observe a high intensity region at the bottom left cavity wall, introduced by waves transmitted through the low attenuation water filled cavity. In the right image the position of the ultrasound probe has been changed to the left of the operating channel, and we observe that the bright rim, or the apparent enhanced echo, is now observed in the bottom right cavity wall.

The present invention is concerned with an aqueous ultrasound contact fluid comprising a pharmaceutical grade triglyceride and a pharmaceutically acceptable emulsifier and optionally a pharmaceutically acceptable humectant as defined in the Patent claims.

DETAILED DESCRIPTION OF THE INVENTION

The term ultrasound contact fluid as used herein means a medium used to exclude air between the ultrasound probe and the tissue, hence the main purpose is to provide acoustic coupling between the ultrasound transducer/probe and the tissue to be investigated. The term is synonymous with terms like "contact fluid", "contact agent", "coupling fluid", "acoustic fluid", "acoustic coupling fluid" and "acoustic coupling agent".

An object of the current invention is to solve the problem encountered in ultrasound imaging, where a difference in signal intensity is observed because the ultrasound is at least partly propagating in media with different attenuation. This results in an ultrasound image in which there are substantial regional differences in signal intensity. This problem makes it difficult to interpret the images and it is difficult to adjust the acquisition parameters to balance the regional differences in signal intensity.

It is another object of the present invention is to solve the problem encountered when inserting a fluid to a body cavity, and there is observable a difference in intensity dependent on whether or not the ultrasound waves have at least partly been propagating in the organ or cavity in which the fluid has been administered.

A further object of the current invention is to solve the problem encountered when inserting a fluid to a body cavity or the cardiac system to enable ultrasound imaging, and the ultrasound images have a highly different intensity at the fluid filled cavity wall and beyond compared to the signal intensities of the tissue adjacent to the cavity.

The present invention concerns an aqueous ultrasound contact fluid which can be use in body cavities or resection cavities during ultrasound imaging, particularly when said ultrasound imaging is carried out during surgery. The composition of the fluid according to the present invention provides attenuation of the acoustic waves equal to the tissue to be examined.

In an embodiment of the invention an aqueous ultrasound contact fluid is provided comprising a pharmaceutical grade triglyceride, a pharmaceutically acceptable emulsifier and optionally a pharmaceutically acceptable humectant wherein triglyceride content is in the range of 8-240 g/1000 ml contact fluid and the amount of emulsifier is 0.4-18 g/1000 ml contact fluid and optionally an humectant in the amount of 1.2-30 g/1000 ml contact fluid.

In another embodiment of the invention an ultrasound contact fluid is provided wherein the triglyceride content is in the range of 10-200 g/1000 ml contact fluid, the amount of emulsifier is 0.5-15 g/1000 ml contact fluid and the optional amount of humectant is 1-25 g/1000 ml contact fluid.

In a further embodiment of the invention an ultrasound contact fluid is provided wherein the amount of triglyceride is 50-110 g/1000 ml contact fluid, the amount of emulsifier is 2-10 g/1000 ml contact fluid and optionally an humectant in the amount of 5-15 g/1000 ml contact fluid.

The pharmaceutical grade triglyceride used may be selected from vegetable oils or animal fats. Vegetable oils may preferably be selected from the group consisting of soybean oil, olive oil, palm oil and copra oil. Examples of animal fats that may be used are milk fats, fish oils and fish liver oils.

The pharmaceutically acceptable emulsifier used may be selected from the group consisting of lecithin (e.g. egg yolk lecithin, soy lecithin), emulsifying wax, cetearyl alcohol, polysorbate 20, and ceteareth 20.

The pharmaceutically acceptable humectant may be selected from the group consisting of glycerol, lactic acid, polyols, propylene glycol, and sorbitol.

For an ultrasound contact fluid to be used in body and resection cavities a pH in the physiological range is necessary, and the pH in the fluid can be adjusted to a pH level suitable for the intended clinical use, for example in the range 6 to 8, preferably about 7, by use of means generally known in the art. Further the fluid according to the invention is a biocompatible and sterile fluid for acoustic examinations/imaging of cavities.

Adjustment of osmolality and salinity of fluids to physiological acceptable values are generally known in the art and such adjustments means are applicable for the present invention.

In a particular embodiment of the present invention the ultrasound contact fluid according to the invention comprises 90 g soybean oil, 5.5 g lecithin and 10 g glycerol and physiological saline water to obtain 1000 ml.

The present invention concerns an aqueous ultrasound contact fluid that can be administered to patients (human or animals) before or during ultrasound examination, which is biocompatible, sterile and has an attenuation coefficient α that is at least a factor 30 larger than the attenuation coefficient for water, (i.e. α>0.066.). In an embodiment of the invention the attenuation coefficient α is in the range of 0.20 to 1.10, preferably 0.80. In an embodiment of the invention the contact fluid has an attenuation coefficient α targeted at 0.80 dB/(MHz·cm), which is in the same order as α of the adult human brain.

Figure 2:
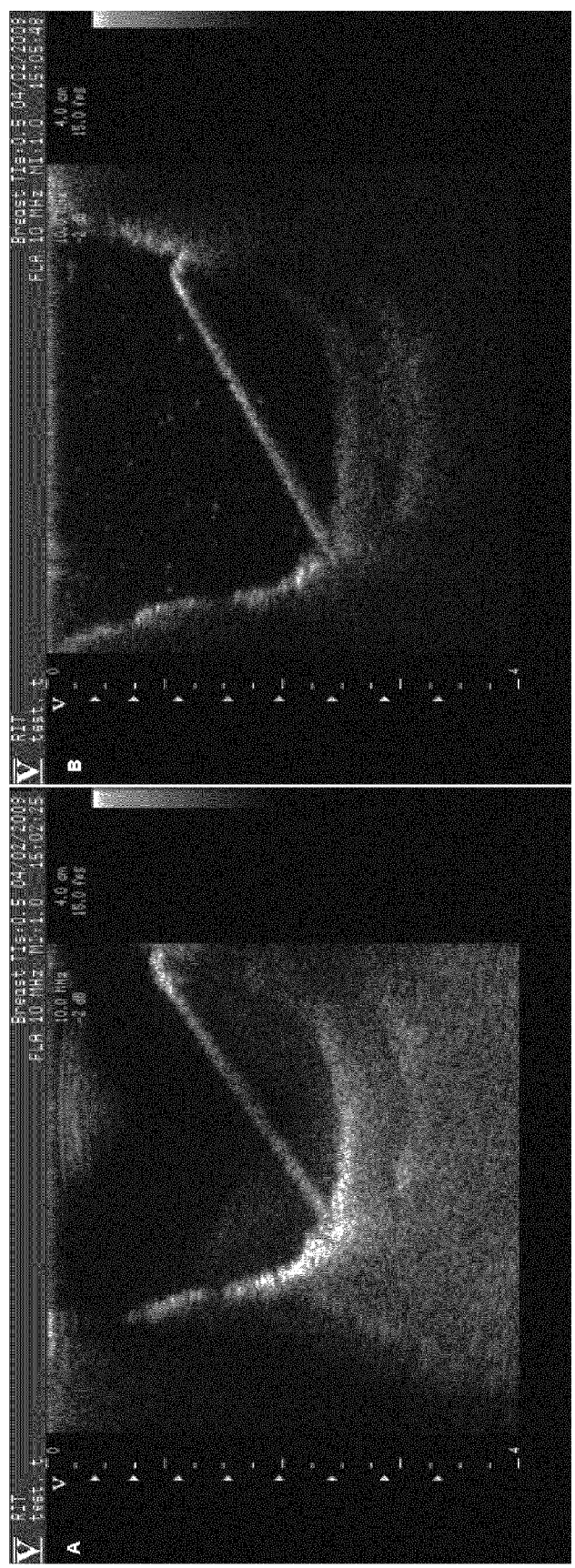
FIG. 2 shows ultrasound imaging of a cavity with dipping reflector when filled with A) NaCl (0.9%) fluid which is representative for fluids applied during brain surgery and B) fluid with attenuation as defined according to the invention.

The effect of the invention is shown in FIG. 2A (prior art) in which a phantom with a cavity is filled with NaCl (0.9%) and a high intensity signal is seen at and below the bottom of the fluid filled cavity. This high intensity signal is partly masking the structures below the bottom of the cavity, and this is also frequently encountered in a clinical situation. In FIG. 2B (present invention) the cavity is filled with a fluid according to the present invention that provides attenuation of the acoustic waves according to the criteria of the invention. It is observed that the dipping structure in the cavity has at least the same intensity as seen in FIG. 2A, while the intensity at the bottom cavity and beyond is reduced in amplitude and more similar to the intensity of the adjacent media

EXAMPLES

Example 1

Figure 3:
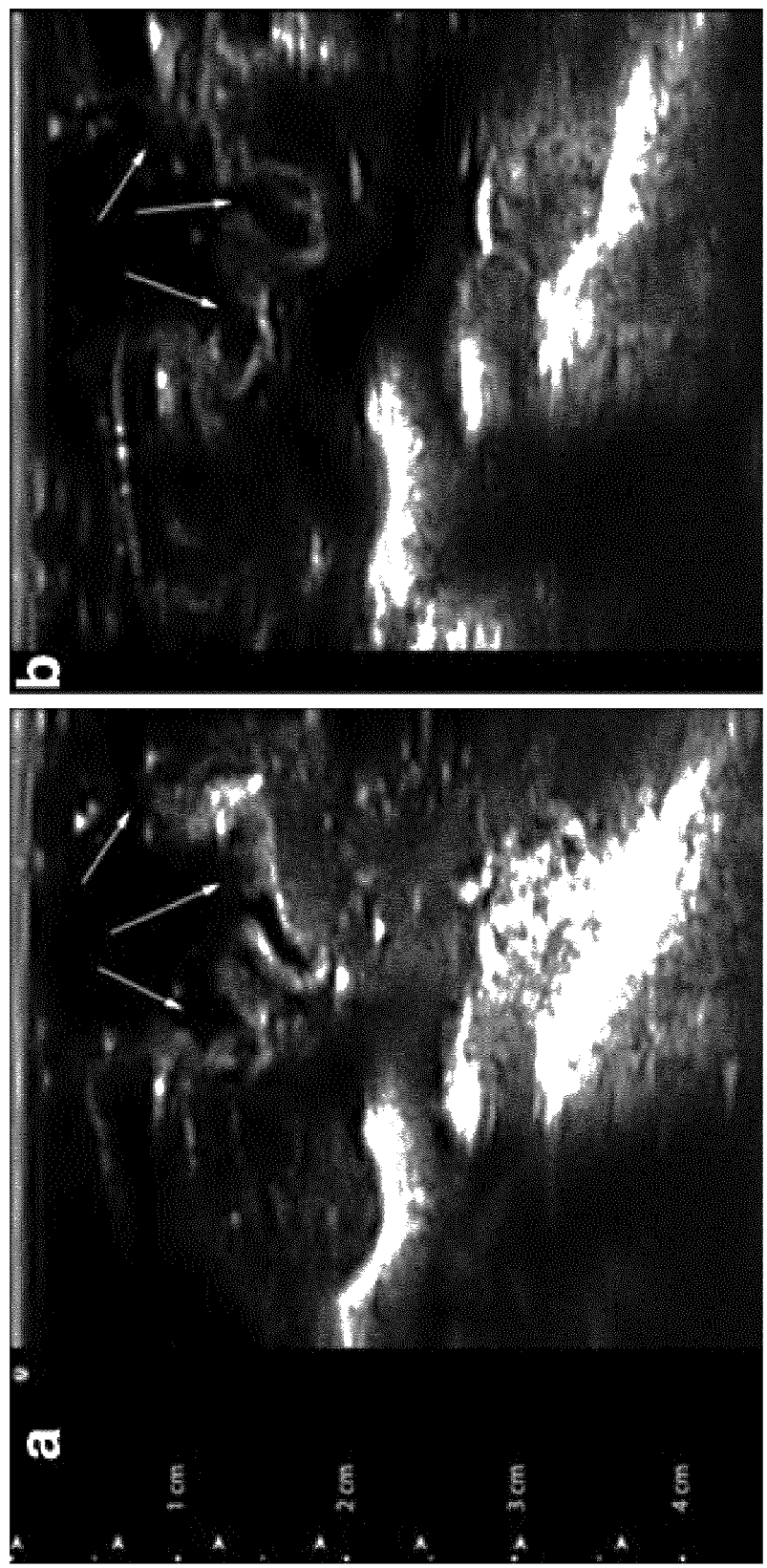
FIG. 3 shows comparison of images of resection cavity in piglet brain using physiological saline (a) and contact fluid according to the present invention (b).

The imaging properties of the contact fluid according to the invention have been evaluated on a phantom (FIG. 2) and on fresh piglet cadavers (FIG. 3).

Phantom

In the phantom a needle is inserted in a cavity made in oasis and imaged by a flat linear array (Vingmed Ultrasound System FiVe). Images were made with a regular saline shown to the left (A) in FIG. 2 and with a contact fluid according to the invention with a higher attenuation shown to the right (B) in FIG. 2. The same acquisition parameters were used, but the global gain was adjusted in each case to provide the "best image" as defined by an experienced ultrasound operator. The bright region below the bottom of the cavity in (A) is almost completely vanished in (B). Thus the image made using a contrast fluid with attenuation in accordance with the present invention gives a more accurate picture without artefacts present in (A).

Piglet Brain

Newly destroyed piglets were used in an experiment comparing imaging quality using saline or a contact fluid according to the present invention. Resection cavity (marked with arrows in FIG. 3) made in a fresh piglet brain imaged using physiological saline to fill the resection cavity (a) and imaged using a contact fluid according to the invention (b). The acquisition parameters are identical in both cases. The dominating signal enhancements in the deeper part of the images are caused by strong reflection from the scull base. The difference in intensity below the resection cavity in the two images (a and b) is pronounced. Even if the slice orientation is not perfectly identical in the images, it is apparent that there is no artificial signal enhancement directly below the bottom of the resection cavity in b. The differences in signal intensity can also be seen in the deeper bone reflections in a and b.

Example 2

An animal study assessing safety of the ultrasound contact fluid according to the invention have been carried out.

8 rats and 6 pigs were included in the study. The rats were included for intraparechymal injection into the brain, and the pigs were included with injection of the contrast fluid into the subarachnoid space. Animal behaviour, EEG registrations, histopathology and immunohistochemistry were evaluated.

In this safety study in rats and pigs no adverse clinical events of the contact fluid according to the present invention for improving image quality in ultrasound-guided operations were detected. Hence, the ultrasound contact fluid according to the invention appears safe under the tested circumstances.

The invention claimed is:

1. A method for intraoperative ultrasound imaging, comprising:
   filling a body cavity with an aqueous ultrasound contact fluid,
      wherein the aqueous ultrasound contact fluid is a composition comprising a pharmaceutical grade triglyceride and a pharmaceutically acceptable emulsifier and optionally a pharmaceutically acceptable humectant,
      wherein the triglyceride content is in the range of 8-240 g/1000 ml contact fluid and the amount of emulsifier is 0.4-18 g/1000 ml contact fluid, and optionally a humectant in the amount of 1.2-30 g/1000 ml; and
   obtaining an ultrasound image of a body region that comprises at least part of the body cavity filled with the aqueous ultrasound contact fluid,
      wherein the aqueous ultrasound contact fluid reduces image artifacts associated with the body cavity.

2. The method according to claim 1,
   wherein the amount of triglyceride is in the range of 10-200 g/1000 ml contact fluid, and
   wherein the amount of emulsifier is 0.5-15 g/1000 ml contact fluid and optionally a humectant in the amount of 1.2-25 g/1000 ml contact fluid.

3. The method according to claim 1,
   wherein the amount of triglyceride is 50-110 g/1000 ml contact fluid, the amount of emulsifier is 2-10 g/1000 ml contact fluid, and
   optionally a humectant in the amount of 5-15 g/1000 ml contact fluid.

4. The method according to claim 1, wherein said triglyceride is vegetable oil.

5. The method according to claim 4, wherein said vegetable oil is selected from the group consisting of soybean oil, olive oil, palm oil, and copra oil.

6. The method according to claim 1, wherein said emulsifier is selected from the group consisting of lecithin, egg yolk lecithin, soy lecithin, emulsifying wax, cetearyl alcohol, polysorbate 20, and ceteareth 20.

7. The method according to claim 1, wherein the humectant is selected from the group consisting of glycerol, lactic acid, polyols, propylene glycol, and sorbitol.

8. The method according to claim 1, wherein the ultrasound contact fluid comprises a pH adjusting additive.

9. The method according to claim 8, wherein an amount of the pH adjusting additive is added to set the pH in the range of 6 to 8.

10. The method according to claim 9, wherein the pH is set to 7.

11. The method according to claim 1, wherein the ultrasound contact fluid comprises 90 g soybean oil, 5.5 g lecithin and 10 g glycerol and physiological saline to obtain 1000 ml.

12. The method according to claim 1, wherein the ultrasound contact fluid has an attenuation coefficient $\alpha > 0.066$.

13. The method according to claim 12, wherein the attenuation coefficient $\alpha$ is in the range of 0.20 to 1.10.

14. The method according to claim 13, wherein the attenuation coefficient $\alpha$ is 0.80.

15. The method according to claim 1, wherein said triglyceride is an animal fat.

16. The method according to claim 15, wherein said animal fat is selected from the group consisting of milk fats, fish oils, and fish liver oils.

\* \* \* \* \*